United States Patent [19]

Rabourn

[11] 4,152,349

[45] May 1, 1979

[54] POLYISOCYANATE COMPOSITIONS

[75] Inventor: Warren J. Rabourn, Deer Park, Tex.

[73] Assignee: The Upjohn Company, Kalamazoo, Mich.

[21] Appl. No.: 880,286

[22] Filed: Feb. 22, 1978

[51] Int. Cl.² ............... C07C 119/048; C07C 125/06; C08G 18/20

[52] U.S. Cl. .......................... 260/453 SP; 252/182; 260/453 AM; 521/159; 528/52; 528/59; 560/26

[58] Field of Search ............ 260/453 SP, 2.5 AC, 260/453 AM; 521/159; 528/52; 560/26

[56] References Cited

U.S. PATENT DOCUMENTS 2,817,663  12/1957  Conlon et al. ............... 260/45.8 NZ
3,914,189  10/1975  Rudner et al. ............... 260/2.5 AC

*Primary Examiner*—Dolph H. Torrence

*Attorney, Agent, or Firm*—Denis A. Firth; John Kekich

[57] ABSTRACT

The reactivity of polymethylene polyphenyl isocyanates containing 20 to 90 percent of methylenebis(phenyl isocyanates) is improved, and stabilized against a decline on storage, by incorporating therein very small amounts of a compound of the formula

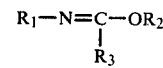

wherein $R_1$=alkyl, aryl; $R_2$=alkyl; $R_3$=H, alkyl or aralkyl; and $R_1$ and $R_2$ taken together represent the residue of an oxazoline or oxazine. 2-Ethyloxazoline is the preferred compound for incorporation in the polyisocyanate.

12 Claims, No Drawings

POLYISOCYANATE COMPOSITIONS

BACKGROUND OF THE INVENTION

1. Field of the Invention

This invention relates to isocyanate compositions and is more particularly concerned with polymethylene polyphenyl polyisocyanates having improved reactivity and storage stability.

It is well recognized in the art that the presence of free hydrogen chloride, and a wide variety of by-products containing hydrolyzable chloride, produced during the preparation of polyisocyanates by phosgenation of the corresponding amines, has an adverse effect on the rate of reaction of said polyisocyanates with active hydrogen-containing materials such as polyols. This is particularly so in the case of polymethylene polyphenyl polyisocyanates, i.e., the products derived by phosgenation of the mixture of polyamines obtained in the acid condensation of aniline and formaldehyde.

Various methods of adjusting the reactivity and or lowering the hydrolyzable chloride content of such polyisocyanates have been described; see, for example, U.S. Pat. Nos. 3,793,362 and 3,912,600 and the prior art which is discussed therein. We have now found that the reactivity of the above type of polyisocyanates can be increased, and the increased level of activity can be maintained over a prolonged period of storage, by use of very minor amounts of a class of compounds not hitherto recognized as useful for this purpose. Further, the use of these compounds to increase reactivity of the polyisocyanate does not affect adversely the other desirable properties of the polyisocyanate or the properties of the products derived therefrom by reaction with active-hydrogen containing compounds.

Certain members of the above class of compounds, namely oxazolines carrying substituents in the 2-position alone or in the 2- and 4-positions simultaneously, have been shown to be catalysts in the reaction of polyisocyanates with polyols; see U.S. Pat. No. 3,914,189. However, it has not previously been recognized that these compounds, when incorporated into isocyanates in lower amounts than those required for catalysis in accordance with the above reference, would enhance and stabilize reactivity of the isocyanate.

SUMMARY OF THE INVENTION

This invention comprises a polyisocyanate composition characterized by improved reactivity which composition comprises a polymethylene polyphenyl polyisocyanate containing from about 20 percent to about 90 percent of methylenebis(phenyl isocyanate) and having incorporated therein a compound of the formula:

$$R_1-N=C-OR_2 \atop R_3 \qquad (I)$$

wherein $R_1$ is selected from the group consisting of lower-alkyl and aryl, $R_2$ represents lower-alkyl, $R_1$ and $R_2$ taken together represent lower-alkylene having 2 to 3 carbon atoms in the chain which, with the

group, forms the residue of a heterocyclic ring containing from 5 to 6 ring atoms and $R_3$ represents a group selected from hydrogen, lower-alkyl and aralkyl; said compound of the above formula being present in said composition in an amount within the range of 0.2 to 2.0 moles per equivalent of acid present in said polyisocyanate as determined by the acid value of the latter.

The present invention also comprises a process for improving the reactivity of a polymethylene polyphenyl polyisocyanate and maintaining said improved reactivity during storage of the polyisocyanate over a prolonged period.

The term "lower-alkyl" means an alkyl radical having from 1 to 8 carbon atoms, inclusive, such as methyl, ethyl, propyl, butyl, pentyl, hexyl, heptyl, octyl and isomeric forms thereof. The term "aryl" means the radical obtained by removing a hydrogen atom from a nuclear carbon atom of an aromatic hydrocarbon containing from 6 to 12 carbon atoms, inclusive. Illustrative of aryl are phenyl, tolyl, xylyl, naphthyl, diphenylyl, and the like. The term "aralkyl" means aralkyl from 7 to 13 carbon atoms, inclusive, such as benzyl, phenethyl, phenylpropyl, naphthylmethyl, benzhydryl and the like. The term "lower-alkylene having 2 to 3 carbon atoms in the chain" means the divalent radical $-C_nH_{2n}-$ having 2 or 3 carbon atoms in the chain separating the valencies, the hydrogen atoms on each of which carbon atoms can be substituted by alkyl but with the limitation that there are no more than 8 carbon atoms in the alkylene radical. Illustrative of lower-alkylene meeting the above requirements are $-CH_2CH_2-$, $-CH_2CH_2CH_2-$,

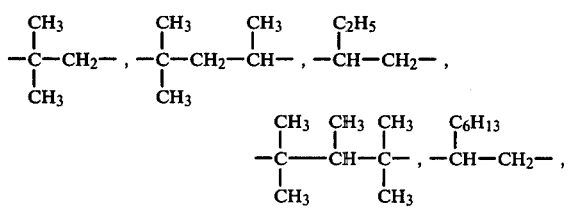

and the like.

DETAILED DESCRIPTION OF THE INVENTION

The compositions of the invention are derived by incorporating the appropriate amount of the compound (I), or a mixture of two or more compounds of formula (I), in the polyisocyanate of which it is to enhance the reactivity. The mixing of the components can be achieved by any of the mixing processes conventional in the art. Since the polyisocyanate is normally a fairly mobile liquid and most of the compounds of formula (I) are also liquid, the admixing is accomplished readily by adding the required amount of compound (I) to the polyisocyanate with appropriate agitation. The admixing can be carried out at ambient temperature (circa 20° C.) or at elevated temperatures up to about 80° C., if desired. In certain instances it is found that, when the mixing of the two components is carried out at elevated temperatures, the degree of enhancement of reactivity of the polyisocyanate which is thereby achieved is greater than the enhancement achieved using the same proportion of compound of formula (I) to polyisocyanate but carrying out the mixing at lower temperatures in the above range.

The admixture of the two components is preferably carried out under conditions which exclude the presence of moisture and of oxygen, e.g., in the presence of an atmosphere of dry inert gas such as nitrogen.

The polyisocyanates which are treated in accordance with the invention are mixtures of polymethylene polyphenyl polyisocyanates containing from about 20 to about 90 percent by weight of methylenebis(phenyl isocyanate), the remainder of the mixture being comprised of oligomeric polyisocyanates of higher molecular weight and functionality. These polymethylene polyphenyl polyisocyanates are well-known in the art and are prepared commercially by phosgenation of mixtures of the corresponding methylene-bridged polyphenyl polyamines. The latter, in turn, are obtained by interaction of formaldehyde, hydrochloric acid and aniline using procedures well-known in the art; see, for example, U.S. Pat. Nos. 2,683,730; 2,950,263; 3,012,088; 3,344,162 and 3,362,979. Included in the polyisocyanates which can be treated in accordance with the invention are modified polymethylene polyphenyl polyisocyanates such as those which have been heat treated in order to increase their viscosity and also those which have been reacted with minor amounts (up to about 0.5 equivalents per equivalent of polyisocyanate) of a polyol to form prepolymers.

The polyols employed in the preparation of said prepolymers can be any of the polyether polyols or polyester polyols known in the art for the preparation of prepolymers of this type. Advantageously, the polyols have an average equivalent weight of about 30 to about 1500 and contain from 2 to 6 hydroxyl groups per molecule. Illustrative of polyols which can be used to prepare prepolymers in accordance with procedures known in the art are those listed in U.S. Pat. No. 3,644,168 (Col. 12, line 17 to Col. 13, line 8). The prepolymers which can be treated in accordance with the present invention are inclusive of those prepolymers of certain polymethylene polyphenyl polyisocyanates and polyethylene glycols of molecular weight from 200 to 600 which prepolymers are described in U.S. Pat. No. 4,055,548.

Illustrative of compounds of the formula (I) are alkyl N-(aryl)imidates such as methyl N-phenylformimidate, ethyl N-phenylformimidate, ethyl N-tolylformimidate, ethyl N-phenylacetimidate, ethyl N-phenylpropionimidate, methyl N-phenylbutyrimidate, ethyl N-(p-tert.-butylphenyl)-formimidate and the like; oxazolines such as 2-methyl-, 2-ethyl-, 2,4,4-trimethyl-, 2-benzyl-, 2-hexyl-, 2-octyl-, 2-ethyl-4-methyl-, and 2-propyl-4,4-dimethyloxazolines and the like; and oxazines such as 2-benzyl-5,6-dihydro-4,4,6-trimethyl-, 6-butyl-5,6-dihydro-2-methyl-, 5,6-dihydro-2,6-dimethyl-, 5,6-dihydro-6,6-dimethyl-, and 5,6-dihydro-2,5,5,6,6-pentamethyl-4H-1,3-oxazine, and the like. All the above compounds and classes of compounds are known in the art and can be prepared by methods well-described in the art.

A preferred group of compounds of formula (I) are the alkyl substituted oxazolines and a particularly preferred species within this group is 2-ethyloxazoline.

As set forth above, the amount of compound (I), or the amount of a mixture of two or more compounds of formula (I), which is incorporated in any given polymethylene polyphenyl polyisocyanate is related to the acid value of the latter. The "acidity" or "acid value," sometimes referred to as the "hot-acidity," of a polyisocyanate is a term well recognized in the art. The acidity is determined by potassium hydroxide titration of the free acid (hydrochloric acid) generated upon subjecting a measured quantity of polyisocyanate to a brief period of heating in methanol; the exact procedure employed is that set forth in U.S. Pat. No. 3,793,362 in Column 7 beginning at line 27. The amount of compound of formula (I), or of a mixture of two or more such compounds, which is incorporated into the polyisocyanate in accordance with the invention is advantageously of the order of 0.2 to 2.0 moles per equivalent of acid present in said polyisocyanate as determined by the acid value of the latter. Preferably the amount of compound of formula (I), or mixture of two or more such compounds, is in the range of 0.4 to 1.2 moles per equivalent of acid present in the polyisocyanate.

The compositions prepared in accordance with the invention possess enhanced reactivity as compared with the corresponding untreated polyisocyanate. Further, the compositons of the invention retain this enhanced level of activity upon storage over prolonged periods of time prior to use in the formation of cellular and noncellular polyurethanes and like polymers which are prepared therefrom. The presence of the compound (I) in the polyisocyanates prepared in accordance with the invention does not have any deleterious effect on the properties of such products prepared therefrom. On the contrary, it is found that, in many instances, the structural strength and related properties of polymers prepared from the polyisocyanates of the invention are superior to those of corresponding polymers prepared from the untreated polyisocyanates.

That the compound (I) is actually increasing the reactivity of the polyisocyanate and not merely acting as a catalyst in the reaction between the polyisocyanate and active-hydrogen containing material is apparent from the following finding. Under identical conditions two polyurethane-forming reactions were carried out. In the one case the polyisocyanate was pretreated with a compound (I) in accordance with the invention before being reacted with the polyol, while in the other case the polyisocyanate was untreated but the compound (I), in the same amount as that used to treat the polyisocyanate, was added to the polyol before reaction with the polyisocyanate. It was found that the cream and tack free times exhibited in the reaction between the polyol and the polyisocyanate which had been treated in accordance with the invention were over 20 times shorter than in the case of the untreated polyisocyanate.

The following examples describe the manner and process of making and using the invention and set forth the best mode contemplated by the inventors of carrying out the invention but are not to be construed as limiting.

EXAMPLE 1

A series of compositions were prepared using as starting material a batch of polymethylene polyphenyl polyisocyanate containing approximately 50 percent by weight of methylenebis(phenyl isocyanate) and having an equivalent weight of 133 and an acid value of 0.05. A portion of the batch was retained as untreated control.

Composition A was prepared by admixing 100 g. of the starting isocyanate with 0.06 g. (representing 0.44 mole per equivalent of acid based on acid value) of 2-ethyloxazoline.

Composition B was made in the same way as Composition A but increasing the amount of 2-ethyloxazoline to 0.12 g. (representing 0.88 mole per equivalent of acid based on acid value).

Composition C was made in the same way as Composition A but increasing the amount of 2-ethyloxazoline to 0.18 g. (representing 1.32 mole per equivalent of acid).

Each of the compositions A-C and the control sample were divided into equal portions and one portion of each was stored at 25° C. under an atmosphere of dry nitrogen for 75 days. The other portion of each sample was stored at 45° C. under an atmosphere of dry nitrogen for the same period.

At the end of the storage period, each sample was submitted to a test for reactivity based on the exothermic temperature generated in a polyurethane forming reaction under standard conditions. The test was carried out as follows:

100 grams of the isocyanate to be tested was added to 100 grams of a proprietary polyol catalyst mixture that does not contain a blowing agent. The combined materials were immediately mixed for 10 seconds at 2000 rpm with a mixing blade (2 inch split Conn type). The material was poured, after mixing, into a 32 ounce paper cup that had been prepared by insertion of thermocouple through its side (¾ inch from bottom with 3 inch immersion). The thermocouple was connected to a temperature recorder to plot temperature versus time. A timer and recorder were started at the beginning of mixing. The slope and amount of exotherm are a measure of the reactivity of the isocyanate. The results obtained in the test are summarized in Table I below.

TABLE I

| Sample | Reaction temperature (after 15 mins.) | |
|---|---|---|
| | After Storage at 25° C. | After Storage at 45° C. |
| Control Composition | 46° C. | 38° C. |
| A Composition | 85° C. | 54° C. |
| B Composition | 109° C. | 95° C. |
| C | 118° C. | 115° C. |

It will be seen from the above results that all of Compositions A, B and C retained markedly greater reactivity (as measured by the exotherm 15 minutes after mixing of the reactants) after storage for 75 days at both 25° C. and 45° C. than did the control samples.

EXAMPLE 2

The procedure described in Example 1 was repeated exactly as described using a different sample of polymethylene polyphenyl polyisocyanate containing approximately 50 percent by weight of methylenebis(phenyl isocyanate). The isocyanate had an equivalent weight of 132.4 and an acid value of 0.06.

Compositions A', B' and C' were prepared by admixing 100 g. of the isocyanate and 0.06 g., 0.12 g., and 0.18 g., respectively of 2-ethyloxazoline corresponding to 0.37, 0.74 and 1.11 moles, respectively, per equivalent of acid in the isocyanate. The samples were divided into two portions, one of which was stored at 25° C. and the other at 45° C. for 75 days as before. At the end of the storage period the samples were all subjected to the reactivity test described in Example 1 and the results are recorded in Table 2.

TABLE 2

| Sample | Reaction temperature (15 mins.) | |
|---|---|---|
| | After Storage at 25° C. | After Storage at 45° C. |
| Control Composition | 33° C. | 30° C. |
| A' Composition | 49° C. | 44° C. |
| B' Composition | 73° C. | 68° C. |
| C' | 103° C. | 94° C. |

Again, it will be seen from the above results that all of Compositions A', B' and C' retained markedly greater reactivity after storage at both temperatures than did the control samples.

EXAMPLE 3

The polyisocyanate used as starting material in preparing the compositions described in this Example was a polymethylene polyphenyl polyisocyanate containing approximately 70 percent by weight of methylenebis(phenyl isocyanate) and having an equivalent weight of 131 and an acid value of 0.05 percent. Five compositions were made by adding the following amounts of 2-ethyloxazoline to 827 g. aliquots of the above isocyanate, the admixture being carried out at room temperature (circa 20° C.).

| Composition | Weight 2-ethyloxazoline | Ratio: | Moles of 2-ethyloxazoline equivs. HCl in isocyanate |
|---|---|---|---|
| D | 0.337 g. | | 0.25 |
| E | 0.674 g. | | 0.5 |
| F | 1.01 g. | | 0.75 |
| G | 1.34 g. | | 1.0 |
| H | 1.68 g. | | 1.25 |

The reactivity of the above compositions and of the untreated polyisocyanate was studied over a period of four months using the following technique. Each isocyanate composition was divided into eight equal amounts and the individual portions were placed in 8 oz. stoppered bottles under nitrogen and stored at room temperature (circa 20° C.) until ready for test. Starting 1 week from initial time of preparation and continuing at weekly intervals for 1 month, then at monthly intervals for four months, one of the bottles in each of the series was checked for reactivity by reacting 100 parts by weight of the polyisocyanate with 133.3 parts by weight of a mixture containing the following ingredients in the specified proportions.

| Polyether triol: MW = 4500 | 100 parts by wt. |
|---|---|
| Ethylene glycol | 19 parts by wt. |
| Dibutyl tin mercaptide | 0.12 parts by wt. |
| Dibutyl tin diacetate | 0.03 parts by wt. |
| Organosilicone surfactant | 1.0 parts by wt. |

The polyisocyanate to be tested and the polyol-catalyst mixture were brought together in a quart paper cup at ambient temperature (circa 20° C.) with high speed mechanical stirring for 10 seconds. The blended material was allowed to react and foam (trapped air introduced in the mechanical mixing causes the foaming) and the cream time, gel time, firm time and tack free time was recorded for each sample. "Cream time" is that time (in seconds), after initial admixture of the polyol and polyisocyanate, at which gas formation of bubble nucleation appears in the mixture. This point in time is usually marked by a pronounced change in color from dark brown to tan. "Gel time" is that time (in seconds) after initial admixture of the polyol and polyisocyanate at which the mixture changes from a strictly fluid to a gel state. "Firm time" is that time (in seconds) after initial admixture of the polyol and polyisocyanate at which the mixture becomes firm to the touch, i.e., surface of the foam is not depressed by applying thumb pressure. "Tack free time" is that time (in seconds) after initial admixture of the polyol and polyisocyanate at which the foam is no longer sticky to the touch.

The determination of the above characteristics of a foam prepared from a polyisocyanate under standard conditions gives a clear indication of the order of reactivity of the polyisocyanate. Observations taken over a period of time on the same polyisocyanate give a measure of the stability of the reactivity upon storage.

The results of such testing for Compositions D–H and for the untreated polyisocyanate are shown in Table 3.

ployed. An aliquot of 827 g. of the polyisocyanate was heated to 70° C. and admixed with stirring at this temperature with 1.01 g. (representing 0.75 mole per equivalent of acid in the polyisocyanate) of 2-ethyloxazoline. The mixture was then cooled to room temperature (20° C.) and divided into 9 equal portions which were placed in 8 oz. stoppered bottles under a nitrogen atmosphere and stored at room temperature. The reactivity of the samples was then checked at intervals over a period of 6 months using the test described in Example 3. The results obtained are shown in Table 4.

TABLE 4

| | Storage Time | | | | | | | | | |
|---|---|---|---|---|---|---|---|---|---|---|
| | Initial | 1 Wk. | 2 Wks. | 3 Wks. | 4 Wks. | 2 months | 3 months | 4 months | 5 months | 6 months |
| cream time (secs) | 19 | 17 | 16 | 16 | 16 | 16 | 15 | 15 | 17 | 13 |
| gel time (secs) | 29 | 19 | 18 | None | 17 | 19 | 16 | 16 | 18 | 15 |
| tack free time (secs) | 37 | 25 | 21 | 24 | 19 | 20 | 17 | 17 | 20 | 18 |
| firm time (secs) | 55 | 45 | 45 | 47 | 45 | 30 | 27 | 30 | 35 | 45 |

It will be seen that the treated polyisocyanate had a high degree of reactivity as compared with the untreated isocyanate (see control; Example 3) and this level of reactivity was maintained on storage over a period of three months. It was also observed that the polyurethane foam prepared from the various samples during the storage period showed significantly less tendency to crack after demolding than did corresponding foams prepared from the various samples of compositions D–H of Example 3.

TABLE 3

| Composition | Storage Time | | | | | | | |
|---|---|---|---|---|---|---|---|---|
| | Initial | 1 Wk. | 2 Wks. | 3 Wks. | 4 Wks. | 2 months | 3 months | 4 months |
| Control | | | | | | | | |
| cream time (secs) | ca 180 | ca 180 | ca 240 | ca 180 | ca 240 | ca 240 | ca 200 | ca 180 |
| gel time (secs) | — | — | — | — | — | — | — | — |
| tack free time (secs) | — | — | — | — | — | — | — | — |
| firm time (secs) | — | — | — | — | — | — | — | — |
| D | | | | | | | | |
| cream time (secs) | 17–19 | 19 | 19 | 19 | 17 | 18 | 23 | 23 |
| gel time (secs) | none | 30 | none | none | none | none | none | none |
| tack free time (secs) | 45 | 47 | 63 | 67 | 55 | 75 | 93 | 60 |
| firm time (secs) | 120 | 120 | 145 | 125 | 125 | 145 | 140 | 150 |
| E | | | | | | | | |
| cream time (secs) | 16 | 16 | 18 | 18 | 16 | 17 | 16 | 16 |
| gel time (secs) | 19 | 19 | 21 | none | 19 | 18 | 19 | 19 |
| tack free time (secs) | 32 | 21 | 24 | 33 | 25 | 21 | 23 | 24 |
| firm time (secs) | 67 | 57 | 67 | 87 | 57 | 60 | 60 | 85 |
| F | | | | | | | | |
| cream time (secs) | 16 | 16 | 18 | 18 | 15 | 16 | 15 | 16 |
| gel time (secs) | 22 | 18 | 19 | 20 | 17 | 18 | 16 | 17 |
| tack free time (secs) | 30 | 20 | 22 | 24 | 19 | 20 | 18 | 18 |
| firm time (secs) | 50 | 37 | 47 | 53 | 37 | 40 | 30 | 25 |
| G | | | | | | | | |
| cream time (secs) | 15 | 15 | 17 | 17 | 16 | 15 | 15 | 16 |
| gel time (secs) | 20 | 19 | 23 | 21 | 19 | 16 | 16 | 17 |
| tack free time (secs) | 25 | 21 | 26 | 25 | 20 | 17 | 19 | 18 |
| firm time (secs) | 45 | 37 | 53 | 53 | 37 | 25 | 25 | 25 |
| H | | | | | | | | |
| cream time (secs) | 15 | 15 | 16 | 14 | 15 | 15 | 14 | — |
| gel time (secs) | 20 | 18 | 17 | 15 | 17 | 17 | 15 | — |
| tack free time (secs) | 33 | 20 | 18 | 16 | 18 | 18 | 16 | — |
| firm time (secs) | 45 | 37 | 37 | 30 | 27 | 25 | 19 | — |

It will be seen from the above results that the reactivity of the untreated polyisocyanate was extremely poor, whereas that of the treated polyisocyanates D–H was good and was maintained at the initial level over a prolonged period of storage.

EXAMPLE 4

The same polymethylene polyphenyl polyisocyanate as that used as starting material in Example 3 was em-

EXAMPLE 5

The polyisocyanate employed as starting material was a prepolymer prepared by reacting 100 parts by weight of a polymethylene polyphenyl polyisocyanate

[containing approximately 70 percent by weight of methylenebis(phenyl isocyanate) and having an equivalent weight of 131] with 12.7 parts by weight of a polyoxyethylene glycol having a molecular weight of 400. The prepolymer had an equivalent weight of 161 and an acid value of 0.04 percent.

Five compositions (I–M) were made by adding the following amounts of 2-ethyloxazoline to 827 g. aliquots of the above prepolymer, the admixture being carried out at room temperature (ca 20° C.).

| Composition | Wt. 2-ethoxazoline | Ratio: | moles 2-ethyloxazoline equivs. HCl in isocyanate |
|---|---|---|---|
| I | 0.112 g. | | 0.25 |
| J | 0.224 g. | | 0.50 |
| K | 0.336 g. | | 0.75 |
| L | 0.45 g. | | 1.0 |
| M | 0.56 g. | | 1.25 |

Each of the above compositions was then divided into eight equal portions which were placed individually under dry nitrogen in 8 oz. stoppered bottles and stored at room temperature until ready for test. The reactivity of the various samples and the untreated prepolymer was checked at intervals over a period of 4 months using the test described in Example 3. The results are shown in Table 5.

cyanate with 2-ethyloxazoline prior to formation of the prepolymer or by treating the already formed prepolymer with 2-ethyloxazoline.

Two isocyanate compositions were prepared as follows using as starting material the same batch of polymethylene polyphenyl polyisocyanate as that used in Example 3.

Composition N

To a portion of 2000 g. of the polyisocyanate, preheated to 70° C., was added with vigorous stirring 3.25 g. of 2-ethyloxazoline (representing 1 mole per equivalent of acid in the polyisocyanate). The mixture was maintained at 70° C. overnight before being cooled to room temperature (ca 20° C.). A portion (1787 g.) of the product was heated to 70° C. and stirred while a total of 155 g. of polyethylene glycol (MW=400) was added. After the addition was complete, the mixture was stirred and heated at 75° C. for 1 hour before being cooled to room temperature.

Composition O

A second portion of 2000 g. of the same polyisocyanate was heated to 70° C. with stirring in a nitrogen atmosphere and a total of 170 g. of polyethylene glycol (MW = 400) was added slowly. When the addition was complete, the mixture was stirred for a further hour at 75° C. and then 3.65 g. (corresponding to 1 mole per equivalent of acid in the starting isocyanate) of 2-

TABLE 5

| Composition | Storage Time | | | | | | | |
|---|---|---|---|---|---|---|---|---|
| | Initial | 1 Wk. | 2 Wks. | 3 Wks. | 4 Wks. | 2 months | 3 months | 4 months |
| Control | | | | | | | | |
| cream time (secs) | >360 | >360 | >360 | >360 | >360 | >360 | >360 | >360 |
| gel time (secs) | — | — | — | — | — | — | — | — |
| tack free time (secs) | — | — | — | — | — | — | — | — |
| firm time (secs) | — | — | — | — | — | — | — | — |
| I | | | | | | | | |
| cream time (secs) | 120 | 83 | 163 | 105 | 87 | 137 | >95 | >120 |
| gel time (secs) | >360 | None | None | None | None | None | None | — |
| tack free time (secs) | — | ca 360 | — | >360 | >360 | >360 | >360 | — |
| firm time (secs) | — | — | — | — | — | — | — | — |
| J | | | | | | | | |
| cream time (secs) | 27 | 33 | 30 | 37 | 33 | 53 | 33 | 35 |
| gel time (secs) | 43 | 43 | 57 | — | 47 | 115 | 43 | None |
| tack free time (secs) | 83 | 87 | 97 | 125 | 57 | 185 | 77 | 100 |
| firm time (secs) | 210 | 210 | 227 | 245 | 235 | 315 | 185 | 215 |
| K | | | | | | | | |
| cream time (secs) | 20 | 23 | 27 | 33 | 20 | 25 | 24 | 22 |
| gel time (secs) | 25 | 30 | 32 | 47 | 24 | 30 | 26 | 25 |
| tack free time (secs) | 35 | 40 | 50 | 95 | 28 | 43 | 32 | 30 |
| firm time (secs) | 75 | 180 | 187 | 245 | 53 | 85 | 80 | 65 |
| L | | | | | | | | |
| cream time (secs) | 18 | 18 | 15 | 20 | 20 | 20 | 23 | 22 |
| gel time (secs) | 23 | 20 | 21 | 22 | 22 | 25 | 25 | 24 |
| tack free time (secs) | 28 | 22 | 24 | 28 | 25 | 35 | 30 | 28 |
| firm time (secs) | 40 | 30 | 30 | 57 | 37 | 85 | 95 | 57 |
| M | | | | | | | | |
| cream time (secs) | 17 | 16 | 15 | 16 | 16 | 18 | 19 | 16 |
| gel time (secs) | 18 | 18 | 18 | 17 | 17 | 19 | 23 | 17 |
| tack free time (secs) | 20 | 20 | 22 | 18 | 18 | 20 | 26 | 18 |
| firm time (secs) | 35 | 30 | 33 | 33 | 33 | 27 | 20 | 35 |

It will be seen that all of Compositions I–M possessed superior reactivity to that of the untreated prepolymer and that the excellent level of reactivity of Compositions J–M was maintained on storage for periods up to 4 months.

EXAMPLE 6

This Example shows that the reactivity of an isocyanate terminated prepolymer can be enhanced in accordance with the invention by treating the initial polyisoethyloxazoline was added with stirring. The resulting mixture was stirred at 75° C. for a further 30 minutes before being cooled to room temperature.

Each of the compositions N and O so obtained was divided into 8 equal portions which were placed in individual 8 oz. stoppered bottles under nitrogen and stored at room temperature. The reactivity of the samples was checked at intervals using the test procedure described in Example 3. The results are recorded in Table 6.

TABLE 6

| Composition | Initial | 1 Wk. | 2 Wks. | 3 Wks. | 4 Wks. | 2 months | 3 months |
|---|---|---|---|---|---|---|---|
| N | | | | | | | |
| cream time (secs) | 14 | 15 | 15 | 17 | 16 | 17 | 16 |
| gel time (secs) | 16 | 16 | 17 | 18 | 17 | 18 | 17 |
| tack free time (secs) | 18 | 17 | 18 | 19 | 18 | 19 | 17 |
| firm time (secs) | 20 | 19 | 19 | 20 | 20 | 20 | 18 |
| O | | | | | | | |
| cream time (secs) | 16 | 15 | 15 | 17 | 18 | 18 | 16 |
| gel time (secs) | 17 | 16 | 17 | 18 | 19 | 19 | 16 |
| tack free time (secs) | 18 | 17 | 18 | 19 | 21 | 20 | 17 |
| firm time (secs) | 19 | 18 | 18 | 20 | 23 | 20 | 19 |

It will be seen that both of compositions N and O showed markedly superior reactivity as compared with the untreated polyisocyanate and the high level of activity was maintained substantially unchanged over a storage period of 3 months.

I claim:

1. A polyisocyanate composition characterized by improved reactivity and comprising a polymethylene polyphenyl polyisocyanate containing from about 20 percent to about 90 percent of methylenebis(phenyl isocyanate) and having incorporated therein a compound of the formula

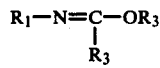

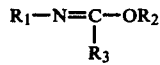

wherein $R_1$ is selected from the group consisting of lower-alkyl and aryl having from 6 to 12 carbon atoms, inclusive, $R_2$ represents lower-alkyl, $R_1$ and $R_2$ taken together represent lower-alkylene having 2 to 3 carbon atoms in the chain which, with the

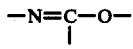

group, forms the residue of a heterocyclic ring containing from 5 to 6 ring atoms, and $R_3$ represents a group selected from hydrogen, lower-alkyl and aralkyl having from 7 to 13 carbon atoms, inclusive, said compound of the above formula being present in an amount within the range of 0.2 to 2.0 moles per equivalent of acid present in said polyisocyanate as determined by the acid value of the latter.

2. A composition according to claim 1 wherein the compound incorporated into said polymethylene polyphenyl polyisocyanate is 2-ethyloxazoline.

3. A composition according to claim 1 wherein said polymethylene polyphenyl polyisocyanate used as starting material contains approximately 70 percent methylenebis(phenyl isocyanate).

4. A composition according to claim 1 wherein said polymethylene polyphenyl polyisocyanate used as starting material contains approximately 50 percent methylenebis(phenyl isocyanate).

5. A composition according to claim 1 wherein said polymethylene polyphenyl polyisocyanate is in the form of a prepolymer obtained by reacting a polymethylene polyphenyl polyisocyanate with a minor proportion of a polyol selected from the class consisting of polyether and polyester polyols and having an average equivalent weight of 30 to 1500 and containing from 2 to 6 hydroxyl groups per molecule.

6. A composition which comprises an isocyanate-terminated prepolymer obtained by reacting a polyisocyanate composition of claim 1 with a minor proportion of a polyol selected from the class consisting of polyether and polyester polyols and having an average equivalent weight of 30 to 1500 and containing from 2 to 6 hydroxyl groups per molecule.

7. A composition according to claim 5 wherein the polyol is a polyethylene glycol of molecular weight about 400.

8. A composition according to claim 6 wherein the polyol is a polyethylene glycol of molecular weight about 400.

9. A polyisocyanate composition characterized by improved reactivity and comprising a polymethylene polyphenyl polyisocyanate containing from about 20 percent to about 90 percent of methylenebis(phenyl isocyanate) and having incorporated therein 2-ethyloxazoline in an amount within the range of 0.2 to 2.0 moles per equivalent of acid present in said polyisocyanate as determined by the acid value of the latter.

10. A polyisocyanate composition according to claim 9 wherein the polymethylene polyphenyl polyisocyanate contains approximately 70 percent by weight of methylenebis(phenyl isocyanate).

11. A composition which comprises the product obtained by reacting a composition according to claim 9 with a minor amount of a polyethylene glycol of molecular weight of about 400.

12. A polyisocyanate composition characterized by improved reactivity and comprising an isocyanate-terminated prepolymer derived by reacting a polymethylene polyphenyl polyisocyanate containing approximately 70 percent by weight of methylenebis(phenyl isocyanate) with a minor amount of a polyethylene glycol of molecular weight about 400, said prepolymer having incorporated therein 2-ethyloxazoline in an amount within the range of 0.2 to 2.0 moles per equivalent of acid present in said prepolymer as determined by the acid value of the latter.

* * * * *

UNITED STATES PATENT OFFICE
CERTIFICATE OF CORRECTION

Patent No. 4,152,349  Dated May 1, 1979

Inventor(s) Warren J. Rabourn

It is certified that error appears in the above-identified patent and that said Letters Patent are hereby corrected as shown below:

| | |
|---|---|
| Column 3, line 18: | Should read: |
| 3,012,088 | 3,012,008 |
| Column 6, line 65: | Should read: |
| formation of | formation or |
| Columns 9 and 10, TABLE 5, last line, Composition M, firm time, 3 months: | Should read: |
| 20 | 30 |

Column 11, Claim 1, line 30:

First formula:

$$R_1-N=C-OR_3$$
$$\quad\quad |$$
$$\quad\quad R_3$$

should be deleted.

Signed and Sealed this

Eighteenth Day of November 1980

[SEAL]

Attest:

SIDNEY A. DIAMOND

Attesting Officer  Commissioner of Patents and Trademarks